United States Patent
Heo et al.

(10) Patent No.: US 10,092,255 B2
(45) Date of Patent: Oct. 9, 2018

(54) INTRAORAL SENSOR

(71) Applicants: Rayence Co., Ltd., Gyeonggi-do (KR); VATECH EWOO Holdings Co., Ltd., Gyeonggi-do (KR)

(72) Inventors: Sung-Kyn Heo, Gyeonggi-do (KR); Jin-Pyo Chun, Gyeonggi-do (KR)

(73) Assignees: Rayence Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 0 days.

(21) Appl. No.: 15/502,566

(22) PCT Filed: Aug. 10, 2015

(86) PCT No.: PCT/KR2015/008349
§ 371 (c)(1),
(2) Date: Feb. 8, 2017

(87) PCT Pub. No.: WO2016/022007
PCT Pub. Date: Feb. 11, 2016

(65) Prior Publication Data
US 2017/0224294 A1    Aug. 10, 2017

(30) Foreign Application Priority Data

| Aug. 8, 2014 | (KR) | 10-2014-0102293 |
| Aug. 8, 2014 | (KR) | 10-2014-0102294 |
| Aug. 8, 2014 | (KR) | 10-2014-0102295 |
| Aug. 8, 2014 | (KR) | 10-2014-0102296 |
| Aug. 8, 2014 | (KR) | 10-2014-0102297 |

(51) Int. Cl.
*A61B 6/14* (2006.01)

(52) U.S. Cl.
CPC .................... *A61B 6/145* (2013.01)

(58) Field of Classification Search
None
See application file for complete search history.

(56) References Cited

U.S. PATENT DOCUMENTS

| 4,734,034 A | 3/1988 | Maness et al. |
| 4,856,993 A | 8/1989 | Maness et al. |
| 6,042,267 A | 3/2000 | Muraki et al. |

(Continued)

FOREIGN PATENT DOCUMENTS

| EP | 1699232 A2 | 9/2006 |
| EP | 2213238 A1 | 8/2010 |

(Continued)

OTHER PUBLICATIONS

Korean Intellectual Property Office, International Search Report of International Application No. PCT/KR2015/008349, dated Nov. 23, 2015.

(Continued)

*Primary Examiner* — Hoon Song
(74) *Attorney, Agent, or Firm* — IP Legal Services, LLC

(57) ABSTRACT

The present invention relates to an intraoral sensor for intraoral X-ray photography, and provides an intraoral sensor bending along an intraoral structure during intraoral X-ray photography, wherein the degree of bending of a first region corresponding to a part facing the major axis differs from that of a second region corresponding to the remaining part.

17 Claims, 12 Drawing Sheets

(56) References Cited

U.S. PATENT DOCUMENTS

| | | |
|---|---|---|
| 2003/0031296 A1 | 2/2003 | Hoheisel |
| 2006/0028546 A1 | 2/2006 | Kokkaliaris et al. |
| 2006/0067462 A1 | 3/2006 | Hack |
| 2006/0262461 A1 | 11/2006 | Wood |
| 2007/0053498 A1* | 3/2007 | Mandelkern ........... A61B 6/145 378/184 |
| 2009/0034687 A1 | 2/2009 | Ayraud |
| 2010/0072379 A1 | 3/2010 | Nishino et al. |
| 2010/0074401 A1 | 3/2010 | Kayzerman |
| 2010/0220839 A1 | 9/2010 | Takagi et al. |
| 2011/0013745 A1* | 1/2011 | Zeller ................... A61B 6/145 378/91 |
| 2012/0291554 A1 | 11/2012 | Baba et al. |

FOREIGN PATENT DOCUMENTS

| | | |
|---|---|---|
| JP | 2006-043465 A | 2/2006 |
| JP | 2006-521130 A | 9/2006 |
| JP | 2011-075390 A | 4/2011 |
| JP | 2013-015347 A | 1/2013 |
| KR | 20-0303670 Y1 | 2/2003 |
| KR | 20-0396821 Y1 | 9/2005 |
| KR | 20-2009-0001520 U | 2/2009 |
| KR | 10-2014-0061177 A | 5/2014 |
| KR | 10-2014-0067257 A | 6/2014 |
| WO | 2009/138331 A1 | 11/2009 |
| WO | 2010/047494 A2 | 4/2010 |

OTHER PUBLICATIONS

Korean Intellectual Property Office, Written Opinion of International Application No. PCT/KR2015/008349, dated Nov. 23, 2015.
Korean Intellectual Property Office, International Search Report of International Application No. PCT/KR2015/004658, dated Aug. 13, 2015.
Korean Intellectual Property Office, International Search Report of International Application No. PCT/KR2015/008347, dated Nov. 6, 2015.
Korean Intellectual Property Office, International Search Report of International Application No. PCT/KR2015/008348, dated Nov. 20, 2015.
Korean Intellectual Property Office, Written Opinion of International Application No. PCT/KR2015/008348, dated Nov. 20, 2015.
Korean Intellectual Property Office, Written Opinion of International Application No. PCT/KR2015/008347, dated Nov. 6, 2015.
European Patent Office, Extended European Search Report of corresponding EP Patent Application No. 15829636.8, dated Apr. 18, 2018.

* cited by examiner

INTRAORAL SENSOR

CROSS REFERENCE TO RELATED APPLICATIONS

This application is a National Stage Patent Application of PCT International Patent Application No. PCT/KR2015/008349 (filed on Aug. 10, 2015) under 35 U.S.C. § 371, which claims priority to Korean Patent Application Nos. 10-2014-0102293 (filed on Aug. 8, 2014), 10-2014-0102294 (filed on Aug. 8, 2014), 10-2014-0102295 (filed on Aug. 8, 2014), 10-2014-0102296 (filed on Aug. 8, 2014), and 10-2014-0102297 (filed on Aug. 8, 2014), the teachings of which are incorporated herein in their entireties by reference.

TECHNICAL FIELD

The present invention relates to an intraoral sensor, and more particularly, to an X-ray intraoral sensor that may be bendable along an intraoral structure during an intraoral X-ray imaging.

BACKGROUND ART

In the conventional approach for intraoral X-ray imagings to obtain X-ray images of teeth and surrounding tissues in the mouth, a film-based method is used.

The film-based method may cause the images to be overly twisted in the mouth and is more likely to lead to image distortion, and is inefficient in terms of time and expense because the film on which the images have been captured needs to be developed and stored. To address this problem, a digital intraoral sensor is widely used these days.

The digital intraoral sensor typically consists of rigid parts, making it inflexible. Although image distortion is less likely to occur during the intraoral scan, this inflexibility gives the patient a foreign or painful feeling.

DISCLOSURE

Technical Problem

Accordingly, the present invention has been made keeping in mind the above problems occurring in the prior art, and an object of the present invention is to provide an intraoral sensor having a property of bendability that has different bending extents in relation to the shape or position of an intraoral structure, such as teeth coming in contact with the intraoral sensor inserted into the mouth for an intraoral X-ray imaging, thereby relieving the foreign and painful feeling felt by the user.

Technical Solution

In accordance with an aspect of the present invention, disclosed is an intraoral sensor for intraoral X-ray imaging, which is bendable along an intraoral structure during an intraoral X-ray imaging, including a first area corresponding to a part along the major axis and a second area corresponding to the remaining parts, wherein the first area and the second area bend to different extents.

The first area may include a center along the major axis, and may bend to a lesser extent than the second area. The first area may occupy 30 to 70% of the entire area. The first area may bend at an angle ranging from 160° to 180° during the intraoral X-ray imaging. The second area may bend at an angle ranging from 110° to 180° during the intraoral X-ray imaging. The intraoral sensor may further include a rear-side support, included in the first area of a rear side, which is opposite the side on which X-rays are incident. The rear-side support may have a form that protrudes from the rear side. The thickness of the intraoral sensor may be 2 to 8 mm, except the rear-side support.

In accordance with another aspect of the present invention, disclosed is an intraoral sensor for intraoral X-ray imaging, including a sensor panel for generating electric signals from X-rays, a first case for covering the side of the sensor panel on which the X-rays are incident, and a housing for covering the sensor panel and the first case, wherein the intraoral sensor is bendable along an intraoral structure during an intraoral X-ray imaging, and has a first area corresponding to a part along the major axis and a second area corresponding to the remaining parts, the first area and the second area bending to different extents.

The sensor panel may include a semiconductor substrate having a thickness of 100 um or less, a photoelectric transducer element formed on the semiconductor substrate, and a scintillator layer that covers the photoelectric transducer element. The intraoral sensor may further include a flexible layer formed in the semiconductor substrate on a side opposite the scintillator layer. The intraoral sensor may further include an elasticity adjustment member, which covers the side of the sensor panel opposite the side on which the X-rays are incident, and a flexible printed circuit board (PCB) that covers the elasticity adjustment member. The intraoral sensor may further include a first adhesive, located between the sensor panel and the elasticity adjustment member, and a second adhesive, located between the elasticity adjustment member and the flexible PCB. The intraoral sensor may further include a rear-side support located on the flexible PCB, wherein the housing covers part or all of the rear-side support. The rear-side support may enable the first area to bend to a lesser extent than the second area by virtue of the position at which it is disposed. The intraoral sensor may further include a transmission cable electrically connected to the flexible PCB through the rear-side support. The intraoral sensor may further include an input/output pad unit, which is provided in the center of the major axis of the flexible PCB along the minor axis and is electrically connected to the transmission cable. The first case may enable the first area to bend to a lesser extent than the second area through its physical shape. The intraoral sensor may further include a rear-side support arranged on the side of the sensor panel opposite the side on which X-rays are incident, and having part or all of the rear-side support covered by the housing. The rear-side support may enable the first area to bend to a lesser extent than the second area through its arrangement position.

Advantageous Effects

According to the present invention, an intraoral sensor may bend to a different extent in relation to the shape or position of an intraoral structure, thereby reducing the discomfort of the patient.

The intraoral sensor may also use a first case, which contains a sensor panel from ahead and has a property of limited bendability. Accordingly, the intraoral sensor bends within a limited range, enabling a bendable X-ray intraoral sensor to be implemented, which may minimize image distortion and relieve the discomfort of the patient to a great extent.

Furthermore, forming grooves in side walls of the first case to control bendability according to the position may help minimize image distortion and may more effectively relieve the discomfort of the patient during an intraoral scan.

Moreover, a rear-side support may be arranged behind the sensor panel to limit the bending extent of the center part of the sensor panel, which is pressed by the rear-side support, in comparison with the surrounding parts of the sensor panel, thereby minimizing image distortion and relieving the discomfort of the patient during an intraoral scan.

In addition, a second case may be used to combine the components of the intraoral sensor more firmly.

Furthermore, a soft molded housing may be used to cover the exterior of the intraoral sensor, thereby significantly relieving the discomfort felt by the patient during an intraoral scan.

Moreover, input/output pads may be arranged to correspond to a central area of a printed circuit board (PCB) having minimal stress applied thereto when bending takes place, such that defects of the input/output pads caused by the bending may be minimized.

Furthermore, grounding patterns may be formed at edges of the PCB and a grounding sheet connected to them may be combined with the sensor assembly, thus leading to the elimination of defects caused by static electricity.

In addition, an X-ray anti-reflection film may be arranged on the back of the sensor panel to alleviate a phenomenon of back-scattering.

Consequently, according to the present invention, an intraoral sensor having a property of limited bendability that helps minimize image distortion may be effectively implemented while simultaneously minimizing the discomfort felt by the patient.

BEST MODE

Embodiments of the present invention will now be described in detail with reference to accompanying drawings.

Figure 1:
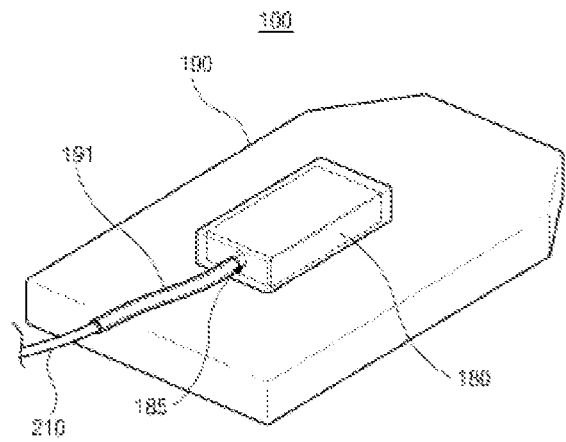
FIG. 1 is a perspective view of an intraoral sensor, according to an embodiment of the present invention.
Figure 2:
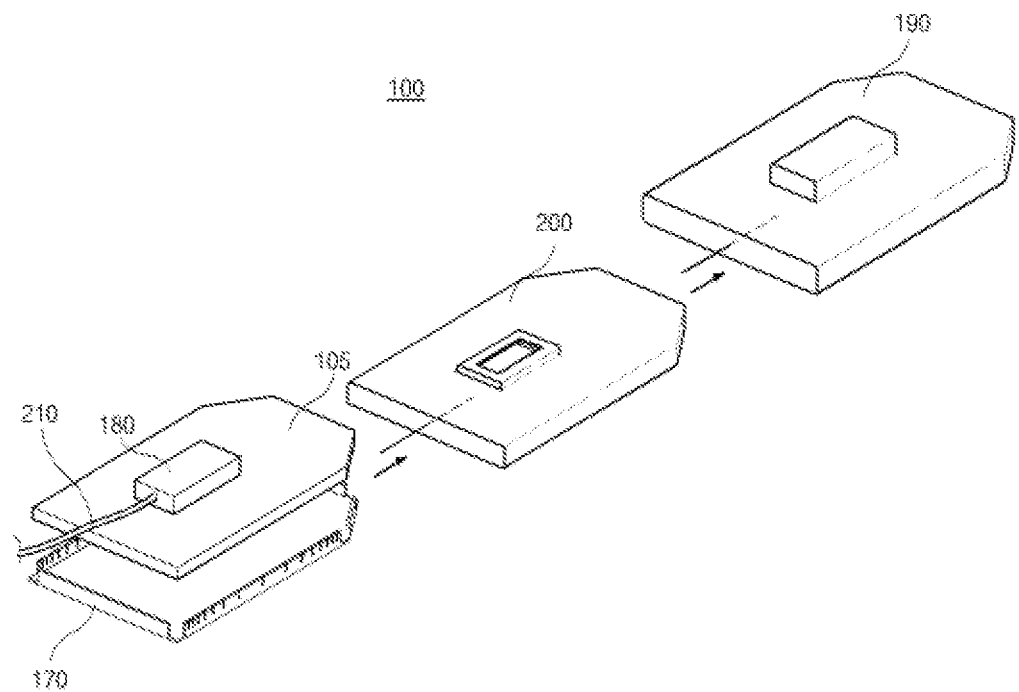
FIG. 2 is an exploded perspective view of the intraoral sensor of FIG. 1.
Figure 3:
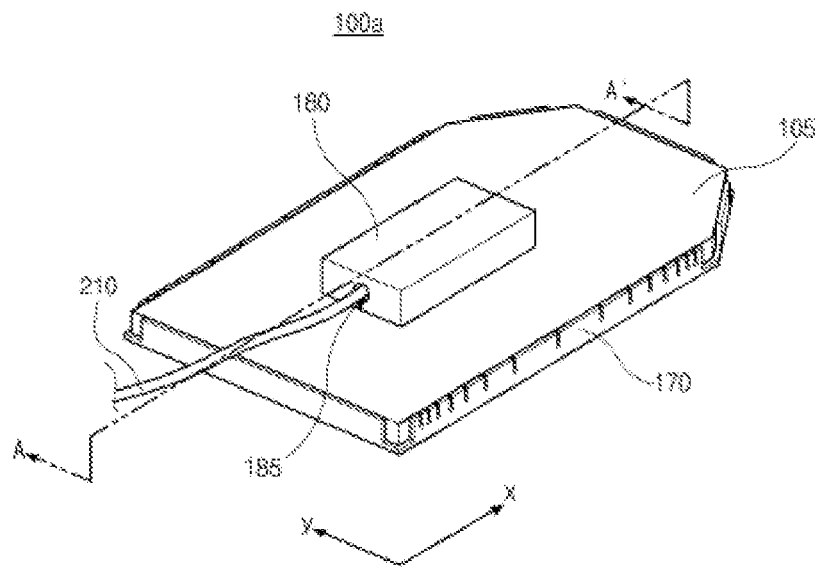
FIG. 3 schematically shows the combined state of a sensor assembly, a first case, and a rear-side support.
Figure 4:
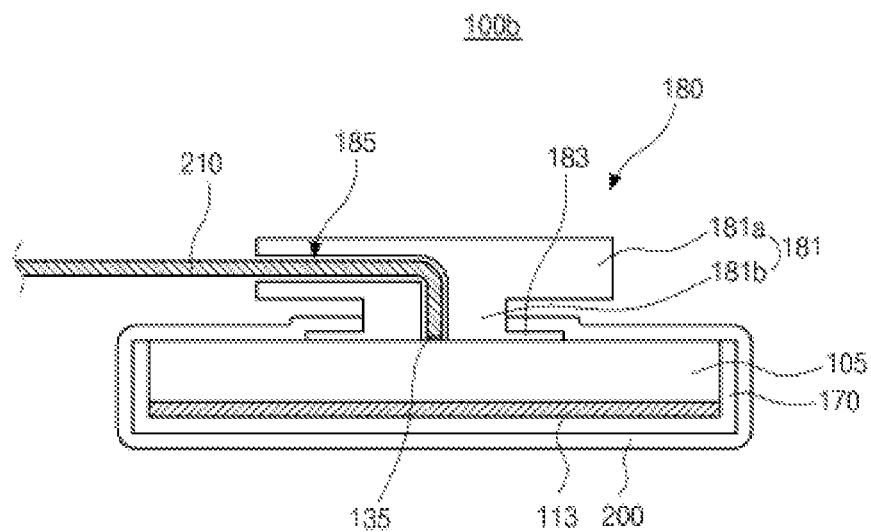
FIG. 4 is a cross-sectional view of the intraoral sensor shown in FIG. 3, cut along line A-A'.

FIG. 1 is a perspective view of an intraoral sensor according to an embodiment of the present invention, FIG. 2 is an exploded perspective view of the intraoral sensor of FIG. 1, FIG. 3 schematically shows the combined state of a sensor assembly, a first case, and a rear-side support, and FIG. 4 is a cross-sectional view of the intraoral sensor shown in FIG. 3, cut along line A-A'. In FIGS. 3 and 4, for convenience of explanation, the structure of an intraoral sensor is shown with a housing 190 left out, and further, in FIG. 3, the structure of the intraoral sensor is shown with a second case 200 left out. The intraoral sensor having the structure of FIG. 3 is given reference numeral 100a and the intraoral sensor having the structure of FIG. 4 is given reference numeral 100b.

Referring to FIGS. 1 to 4, an intraoral sensor 100 in accordance with an embodiment of the present disclosure may include a sensor assembly 105 for detecting X-rays and generating electric signals, a first case 170 located in front of the sensor assembly 105 (i.e. on the side onto which X-rays are incident), and a rear-side support 180 located behind the sensor assembly 102 (i.e. on the side opposite the side on which X-rays are incident).

In the meantime, the intraoral sensor 100 may further include a second case 200 that combines and modularizes the sensor assembly 105, the first case 170, and the rear-side support 180, and a housing 190 that covers and wraps the second case 200.

Figure 5:
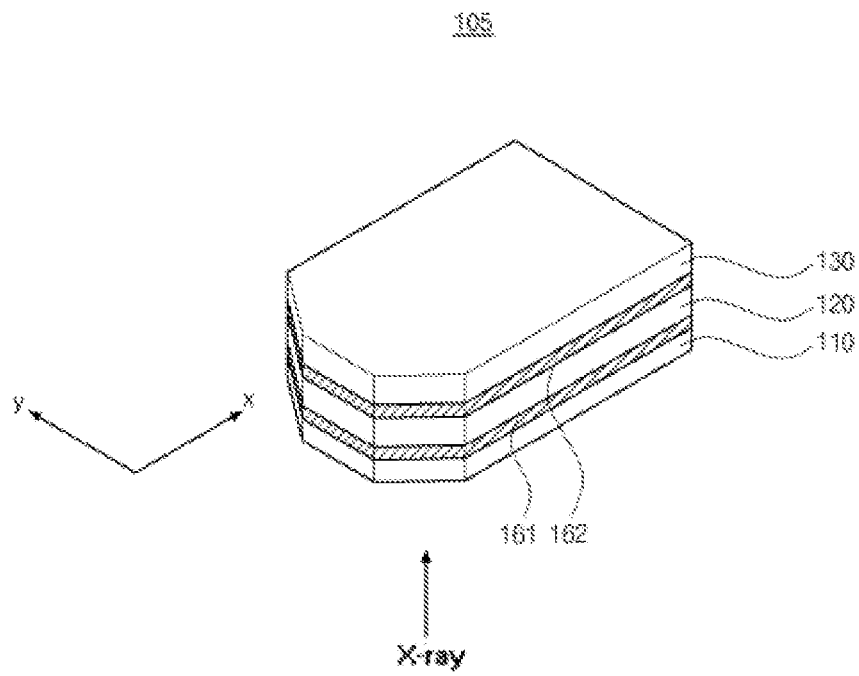
FIG. 5 is a perspective view schematically illustrating a sensor assembly according to an embodiment of the present invention.

The sensor assembly 105 will be described in more detail in connection with FIG. 5. FIG. 5 is a perspective view schematically illustrating the sensor assembly 105 according to an embodiment of the present invention.

Referring to FIG. 5, the sensor assembly 105 may include a sensor panel 110, an elasticity adjustment member 120, and a printed circuit board (PCB) 130. The sensor panel 100, elasticity adjustment member 120, and PCB 130 may be arranged in the direction of X-ray propagation, without being limited thereto.

In the sensor panel 110, a number of pixels are arranged in rows and columns to form a matrix in an effective area, i.e., an active area for the acquisition of X-ray images. A photoelectric transducer element, such as one comprising a photo diode and a switching element, are arranged for each pixel to convert incident light into electric signals and transmit the electric signals. In the meantime, although not shown, pads may be formed on one side of the sensor panel 110 to output the electric signals, and the switching element may be implemented as a complementary metal-oxide semiconductor (CMOS) transistor or a thin film transistor (TFT).

To realize the bendable property of the intraoral sensor 100, the sensor panel 100 may also be formed to be bendable, and for this, the sensor panel 110 may use a fragile substrate formed of e.g. semiconductor, ceramic, glass, or the like, which is 100 um thick or less, for example, 30 to 70 um thick, for the semiconductor substrate. With the substrate formed to this thickness, the sensor panel 110 may have the optimum bending strength.

To form the sensor panel 110 having this thickness, for example, a method for removing a certain thickness of material from the rear side of the substrate may be used. Specifically, on the other side, opposite the side on which the photoelectric transducer is formed, a process such as mechanical grinding, chemical polishing, plasma etching, etc., may be performed to form the substrate to the thickness described above.

In the meantime, as for the sensor panel 110, a sensor panel using a direct conversion scheme for directly converting incident X-rays into electric signals, or a sensor panel using an indirect conversion scheme for converting incident X-rays into visible radiation, which is in turn converted into electric signals, may be used.

Figure 6:
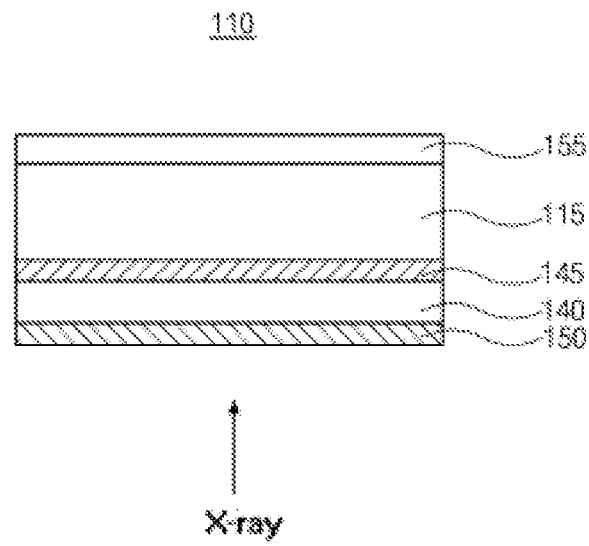
FIG. 6 is a cross-sectional view schematically illustrating a sensor panel according to an embodiment of the present invention.

If the sensor panel 110 of the indirect conversion scheme is used, referring to FIG. 6, showing a cross-sectional view of the sensor panel 100 in accordance with an embodiment of the present invention, a scintillator layer 140 for converting X-rays to visible rays may be formed on one side of a substrate 115 of the sensor panel 110, i.e., on the photoelectric transducer element.

Although FIG. 6 shows an example where the scintillator layer 140 is formed on the side of the sensor panel 110 on which X-rays are incident, the scintillator layer 140 may be formed on the side opposite the side on which the X-rays are incident in another example.

For example, the scintillator layer 140 may be adhered to the substrate 115 using an adhesive 145. Furthermore, on the scintillator layer 140, a protective film 150, which is transparent to radiation, may be formed to protect the scintillator layer 140. The adhesive 145 may use a very soft adhesive that is highly transparent to light, e.g., an Optically Clear Adhesive (OCA) film, and the protective film 150 may use a film comprising a resin material with high radiation transmittance and high humidity-blocking performance. For reference, the adhesive 145 of the OCA film may be 5 to 50 um thick, preferably 10 to 40 um thick, to mitigate the brittleness of the substrate.

In the meantime, for the scintillator layer 140, a CsI based scintillator or Gadox (Gadox: Gd2O2: Tb)-based scintillator may be used.

In an embodiment of the present invention, since the intraoral sensor 100 is formed to have the bendable property, a Gadox-based scintillator may be more appropriately used than a CsI-based scintillator. Since the Gadox-based scintillator has a corpuscular structure, when the intraoral sensor 100 is bendable, the intraoral sensor 100 is less likely to break, thereby avoiding defects. Furthermore, the scintillator layer 140 using Gadox has the advantage of being easily manufactured.

For reference, the scintillator layer 140 using Gadox may be 50 to 300 um thick, and preferably 70 to 200 um thick, in order to obtain sufficient intensity of radiation, in which case a separate protective film, which is highly transparent to radiation and has high performance of blocking humidity, may be added between the scintillator layer 140 and the adhesive 145 to protect and support the scintillator layer 140. For reference, the overall thickness, including the scintillator layer 140, the protective film 150, and the separate protective film, may be 250 to 500 um, and preferably 300 to 450 um, without being limited thereto.

Moreover, a flexible layer 155 may be formed on the other side of the substrate 115 where the scintillator layer 140 is formed, and the flexible layer 155 may be formed of a flexible resin material, e.g. polyimide PI. The flexible layer 155 may have a thickness of, for example, 50 to 150 um, sufficient to mitigate the brittleness of the sensor panel 100, especially the substrate 115, and to prevent breakage in the event of bending of the intraoral sensor 110. The flexible layer 155 may be adhered to the substrate 115 with a predetermined adhesive material, e.g., Die Attach Film (DAF), and the thickness of the adhesive material may be 10 to 30 um or so.

Turning back to FIG. 5, the PCB 130, which is a circuit panel, is located behind the sensor panel 110, and is electrically connected to one side of the sensor panel 110 in order to receive an electric signal from the sensor panel 110 and to send a driving signal to the sensor panel 110.

As the PCB 130, a so-called "flexible PCB", made of a flexible material, may be used to realize the bendable property of the sensor assembly 110.

Figure 7:
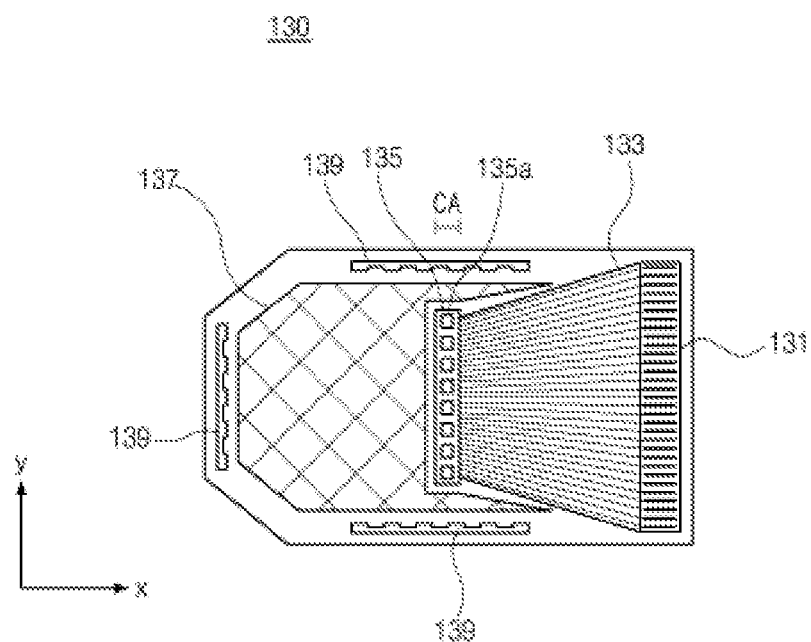
FIG. 7 is a plan schematically illustrating a printed circuit board (PCB) according to an embodiment of the present invention.

In this regard, referring to FIG. 7, showing a plan view schematically illustrating the PCB 130 in accordance with an embodiment of the present invention, a panel connection pad unit 131, a conductive wire pattern unit 133, and an input/output pad unit 135 may be formed on the PCB 130.

As shown in FIG. 7, the panel connection pad unit 131 may be formed on one side of the PCB 130, on which a number of pads are formed. The pads of the panel connection pad unit 131 are electrically connected to corresponding pads formed on one side of the sensor panel 110, i.e. the substrate 115, by wire bonding, by soldering, or using Anisotropic Conductive Film (ACF) or the like, for transmitting electric signals from the sensor panel 110.

In the conductive wire pattern unit 133, multiple wire patterns are formed to connect the panel connection pad unit 131 and the input/output pad unit 135, located at either end of the conductive wire pattern unit 133. One end of the wire pattern is connected to the panel connection pad unit 131 and the other end is connected to the input/output pad unit 135 to transmit signals.

The input/output pad unit 135 is arranged such that it is connected directly or indirectly to the transmission cable (see 210 of FIGS. 1 to 4) to transmit electric signals to the outside. In an embodiment of the present invention, for convenience of explanation, it is assumed that the input/output pad unit 135 is directly connected to the transmission cable 210. In this case, the transmission cable 210 may be connected to the input/output pad unit 135 in various ways, e.g. by soldering, using a connector, or using a conductive film.

In another example, a flexible soft circuit film may be attached onto the back of the PCB 130, and the soft circuit film may include bumps that come into contact with the input/output pad unit 135. In this case, the transmission cable 210 may be connected to the soft circuit film, and may be electrically connected to the input/output pad unit 135 through the soft circuit film. The soft circuit film may be formed to have a smaller area than the PCB 130.

In the present invention, it is preferable that the input/output pad unit 135 be formed to be elongate along the minor axis across the center area CA of the sensor assembly 105. In other words, input/output pads 135a may be arranged in the center area CA while being defined along the minor axis of the PCB 130.

In this regard, in the case where the sensor assembly 105 is shaped like a rectangle in an x-y plane, being longer along the x-axis than along the y-axis, the sensor assembly 105 may be formed to have greater bendability along the x-axis (which is the main axis) than along the y-axis (which is the minor axis), taking into account various factors, such as relief of the discomfort of the patient. That is, it is preferable that the extent of bending forward or backward along the x-axis be greater than that along the y-axis.

At this time, the center area CA of the sensor assembly 105 with respect to the x-axis is the part that is subjected to the smallest amount of stress when bending takes place. Accordingly, if the input/output pad unit 135 is arranged along the y-axis in the center area CA of the x-axis, the stress and displacement applied to the input/output pad unit 135 may be minimized, leading to minimization of defects of the input/output pad unit 135 caused by bending.

In the meantime, a metal thin film 137, electrically isolated from the panel connection pad unit 131, conductive wire pattern unit 133, and input/output pad unit 135, may be formed on one side of the PCB 130. The metal thin film 137 may be made of copper Cu, but is not limited thereto. Furthermore, the metal thin film 137 may be formed in a mesh pattern, but is not limited thereto.

The metal thin film 137 may be formed on at least a part of an area except the area in which the panel connection pad unit 131, the conductive wire pattern unit 133, and the input/output pad unit 135 are formed. At this time, if necessary, the metal thin film 137 may be formed over the entire area of another layer in the PCB 130, which is isolated from the panel connection pad unit 131, the conductive wire pattern unit 133, and the input/output pad unit 135, and may thus serve to alleviate back scattering, as will be described later. In this case, the metal thin film 137 may be made of a metal having a high atomic number, such as W or Ti.

The metal thin film 137 may serve as a means of grounding and electromagnetic interference (EMI) shielding for the PCB 130.

In particular, the metal thin film 137 may further serve as a means of controlling the bendability of the PCB 130.

In this regard, without the metal thin film 137, there is a big difference in the extent of bending between the area where the panel connection pad unit 131, the conductive wire pattern unit 133, and the input/output connection pad unit 135 are formed and the remaining area, but with the metal thin film 137 formed, the difference may be reduced, making the overall extent of bending of the PCB 130 uniform across all areas. The extent of bending of the PCB 130 may be adjusted by varying the material, formation area, thickness, etc., of the metal thin film 137.

Furthermore, in the back of the PCB 130, grounding patterns 139 made of a metal material may be formed along the edges while being exposed to the outside. The grounding patterns 139 may serve as grounding terminals of the PCB 130 together with the metal thin film 137, thereby preventing malfunctions of the intraoral sensor 100 that might be caused by static electricity.

Figure 8:
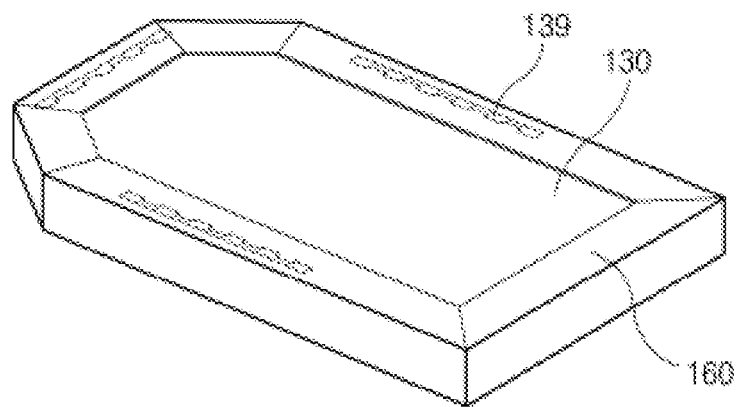
FIG. 8 is a perspective view schematically illustrating a sensor assembly combined with metal sheets according to an embodiment of the present invention.

To improve the discharging ability of the grounding patterns 139, the intraoral sensor 100 may include a metal sheet 160 that comes into contact with the grounding patterns 139. In this regard, referring now to FIG. 8, the metal sheet 160 may be formed to wrap the entirety of the front and sides of the sensor assembly 105, and particularly, cover the back edges of the sensor assembly 105, i.e., the back edges of the PCB 130. Accordingly, the grounding patterns 139 may come in contact with the metal sheet 160, enabling static electricity to come into the metal sheet 160 through the grounding patterns 139, thereby mitigating defects caused by the static electricity.

The metal sheet 160 may be formed of a metal material, which is transparent to radiation, e.g., Au, Al, etc., without being limited thereto. The sensor assembly 105 combined with the metal sheet 160 may be formed to be received in the first case 170.

In the embodiment of the present invention, a PCB 130 having a size corresponding to the sensor panel 110 was used. In another embodiment, a PCB 130 formed to be smaller than the sensor panel 110 and substantially including the panel connection pad unit 131, the conductive wire pattern unit 133, and the input/output pad unit 137, but no metal thin film 137, may be used. For reference, the thickness of the PCB 130 in an embodiment of the present invention may be 150 to 400 um, preferably 200 to 350 um, without being limited thereto.

Figure 9:
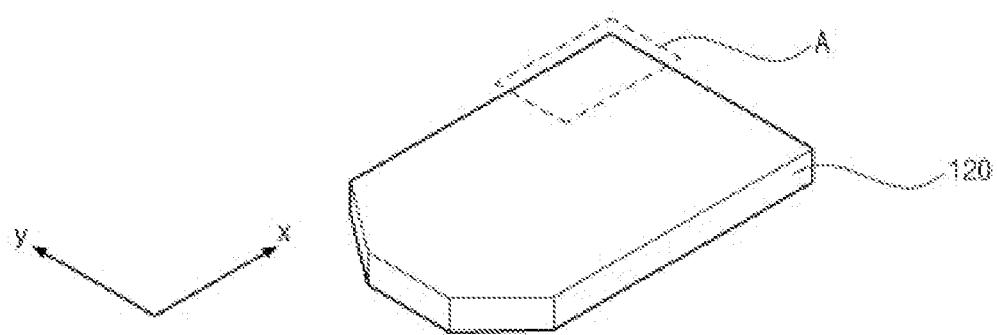
FIG. 9 is a perspective view schematically illustrating an elasticity adjustment member according to an embodiment of the present invention.

The elasticity adjustment member 120 will be described in more detail in connection with FIG. 9. The elasticity adjustment member 120 may be located, for example, between the sensor panel 110 and the PCB 130, and may have a shape corresponding to the sensor panel 110 and may be formed to cover the whole rear side of the sensor panel 110. The elasticity adjustment member 120 may be made of an elastic material having elasticity equal to or greater than that of the sensor panel 110 or the PCB 130. With this configuration, the elasticity adjustment member 120 may allow the sensor assembly 105 to have bendability and restorability within the limit of elasticity of the elasticity adjustment member 120, as well as reduce the brittleness of the sensor panel 110 to protect the sensor panel 1110 against bending of the sensor assembly 105 by controlling the extent of bending of the sensor panel 110 and the PCB 130, i.e., controlling the elasticity of the sensor panel 110 and PCB 130 to less than the bending extent of the elasticity adjustment member 120, that is, to more than the elasticity thereof.

For example, although there may be a difference in elasticity between the components depending on their sizes, thicknesses, or the like, assuming that the sensor panel 110 and the PCB 130 have arbitrary first and second elasticities, respectively, and given that the sensor panel 110 has the structure and thickness shown in FIG. 2, the first elasticity is typically equal to or greater than the second elasticity. Furthermore, the elasticity adjustment member 120 is made of an elastic material having third elasticity, which is equal to or greater than the first elasticity, and accordingly, the elasticity adjustment member 120 may then serve to make the sensor assembly 105 bendable within the elasticity limit of the elasticity adjustment member 120 by setting the elasticity of the sensor panel 110 and PCB 130 to the third elasticity or more and to make the oral sensor device 100 return to its original shape when the external force is eliminated after the intraoral sensor 100 is bendable within the elasticity limit of the elasticity adjustment member 120.

For this, the elasticity adjustment member 120 may use a resin material, particularly a complex mixture of more than two types of substances, and preferably, a complex resin substance including a reinforcing material and a resin.

Furthermore, when superficially observed, the elasticity adjustment member 120 may have different bending properties in the first direction and the second direction, perpendicular to the first direction.

In this regard, for example, in the case where the sensor assembly 105 is shaped like a rectangle in an x-y plane, being longer along the x-axis than along the y-axis, the elasticity adjustment member 120 may be formed to have greater bendability along the x-axis (as the main axis) than along the y-axis (as the minor axis). Even if the sensor assembly 105 is substantially shaped like a square, it may also be formed to have different bending properties for the x- and y-axes.

With the bending properties, the sensor assembly 105 may be bendable more easily along the major axis than along the minor axis, thereby effectively relieving the discomfort of the patient using the sensor assembly 105 during an intraoral scan.

In this regard, during the intraoral scan, the patient may experience discomfort due to the edges of the sensor assembly 105, and in particular due to the ends of the major axis. Accordingly, forming the sensor assembly 105 to have greater bendability along the major axis may significantly help relieve the discomfort felt by the patient.

Furthermore, since the bendability along the x-axis, which is the major axis, is greater than that along the y-axis, which is the minor axis, torsional stress may be distributed along the x- and y-axes, and most of the torsional stress may be converted to stress along the x-axis to thus prevent breakage of the sensor panel 110, in particular the substrate 115.

As described above, the elasticity adjustment member 120 having different bending properties in different directions in the plane may be made of a complex resin material, e.g., fiber-reinforced polymer (FRP) including a fiber reinforcing material. FRP is a substance in which an inorganic fiber, such as glass fiber, carbon fiber, boron fiber, etc., or an organic fiber, such as aramid fiber, polyester fiber, Kevlar fiber, etc., is included as a reinforcing substance in a thermoset resin, such as unsaturated polyester, epoxy, phenol, polyimide, etc., or a thermoplastic resin, such as polyamide, polycarbonate, ABS, PBT, PP, SAN, etc.

Figure 10:
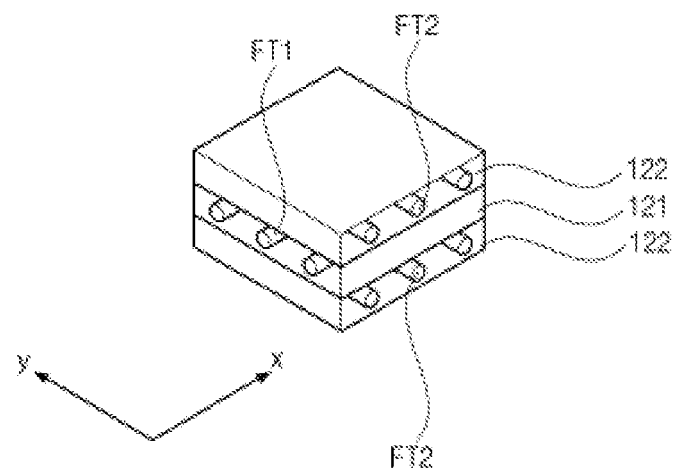
FIG. 10 is an expanded view of part "A" of FIG. 6, schematically illustrating a part of the elasticity adjustment member.

The elasticity adjustment member 120 will be described in more detail in connection with FIG. 10. FIG. 10 is an expanded view of part 'A' of FIG. 9, schematically illustrating a part of the elasticity adjustment member 120, which is a cross-section of the elasticity adjustment member 120.

Further referring to FIG. 10, in the elasticity adjustment member 120, a first thread layer 121, on which first threads (FT1) are arranged in a first direction, the direction of the x-axis, and a second thread layer 122, on which second threads (FT2) are arranged in a second direction, the direction of the y-axis, are alternately arranged in the thickness direction while being impregnated in the resin substance. The first and second threads FT1 and FT2 may each be formed by gathering and weaving the aforementioned fiber in one direction.

Especially, in FIG. 10, the number of first thread layers 121 arranged along the x-axis, the major axis, is less than the number of second thread layers 122 arranged along the y-axis, the minor axis, and FIG. 10 shows an example where one first thread layer 121 and two second thread layers 122 are arranged, for convenience of explanation. The first and second thread layers FT1 and FT2 are made of carbon materials, and the elasticity adjustment member 120 in accordance with an embodiment of the present invention may use CFRP.

As such, with the first thread layers 121 arranged along the major axis in a smaller number than the number of second thread layers 122 arranged along the minor axis, the direction of the major axis has relatively low elasticity, i.e., high bendability, while the direction of the minor axis has relatively high elasticity, i.e., low bendability.

The ratio of elasticity in the direction of the major axis to that of the minor axis is approximately 1:1.5 to 1:6. The elasticity adjustment member 120 may be formed to a thickness of about 100 to 400 um, preferably, 150 to 300 um.

With the different number of thread layers 121, 122 arranged in alternate directions relative to each other in the form described above, an elasticity adjustment layer 120 having higher bendability along the major axis than along the minor axis may be implemented.

Figure 11:
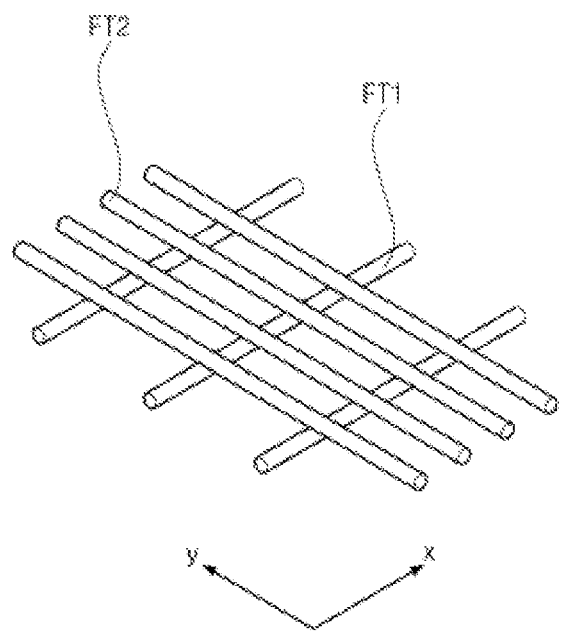
FIG. 11 is a partially enlarged perspective view schematically illustrating a part of the elasticity adjustment member according to an embodiment of the present invention.

FIG. 11 is a partially enlarged perspective view schematically illustrating a part of the elasticity adjustment member 120, according to an embodiment of the present invention, which is different in structure from the elasticity adjustment member 120 of FIG. 10. Referring to this, the resin substance is impregnated with FT1, arranged in the first direction along the x-axis, and with FT2, arranged in the second direction along the y-axis, alternating with each other, and especially, the density of FT1 arranged in the direction of the x-axis, i.e., the major axis, is lower than the density of FT2 arranged along the y-axis, i.e., the minor axis, that is, the arrangement interval of FT1 is wider than the arrangement interval of FT2. The first and second thread layers FT1 and FT2 are made of carbon materials, and the elasticity adjustment member 120 in accordance with an embodiment of the present invention may use CFRP.

As such, with the density of FT1 in the direction of the major axis lower than that of FT2 in the direction of the minor axis, the direction of the major axis has relatively low elasticity, i.e., high bendability, while the direction of the minor axis has relatively high elasticity, i.e., low bendability.

Similar to what is described above, the ratio of the elasticity of the major axis to the elasticity of the minor axis may be approximately 1:1.5 to 1:6. The elasticity adjustment member 120 may be formed to a thickness of about 100 to 400 um, preferably 150 to 300 um.

With the different densities of FT1 and FT2 alternating with each other as described above, an elasticity adjustment layer 120 having higher bendability along the major axis than along the minor axis may be implemented.

In the meantime, as shown in FIG. 5, the elasticity adjustment member 120 may be combined with the sensor panel 110 and the PCB 130, located in front and back of the elasticity adjustment member 120, respectively, using adhesives 161, 162. For convenience of explanation, the adhesive 161 between the elasticity adjustment member 120 and the sensor panel 110 is called a first adhesive 161, and the adhesive 162 between the elasticity adjustment member 120 and the PCB 130 is called a second adhesive 161.

The first and second adhesives have high softness and may, by way of example, be optically clear adhesives (OCAS).

With the use of the first and second adhesives 161 and 162 having high softness, inter-layer stress, produced when the intraoral sensor 100 is bendable, may be effectively relieved.

In this regard, the sensor panel 110, the elasticity adjustment member 120, and the PCB 130 are separate configurations having different properties, in particular having different tensile properties. Accordingly, while the intraoral sensor is bending, there occurs a difference in displacement between the different components, leading to the occurrence of tensile stress. In this case, owing to the use of the soft adhesives 161, 162 between the different components, the tensile stress may be effectively relieved.

Taking into account various general properties, the first and second adhesives 161, 162 may be formed of an OCA film having a thickness of, for example, about 30 to 150 um.

In the sensor assembly 105 in accordance with an embodiment of the present invention, an X-ray anti-reflection film may be arranged on the back of the sensor panel 110 to alleviate a so-called "phenomenon of back scattering", where X-rays are reflected from behind and incident onto the sensor panel 110.

Figure 12:
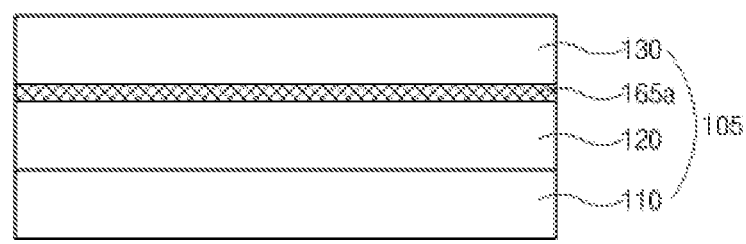
FIGS. 12 and 13 are cross-sectional views schematically illustrating an X-ray anti-reflection film arranged on a sensor assembly according to embodiments of the present disclosure.
Figure 13:
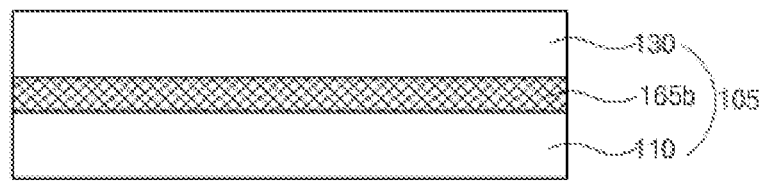

In this regard, reference may be made to FIGS. 12 and 13, which are cross-sectional views schematically illustrating an X-ray anti-reflection film arranged on the sensor assembly 105, according to embodiments of the present disclosure.

FIG. 12 illustrates an X-ray anti-reflection film 165a arranged on one side of the PCB 130, namely the front side thereof, and FIG. 13 illustrates an X-ray anti-reflection film 165b arranged in the place of the elasticity adjustment member 120.

The X-ray anti-reflection film 165a, 165b has a property of absorbing X-rays that have passed through the sensor panel 110 among incident X-rays, thereby preventing the X-rays from being incident onto the sensor panel 110. Accordingly, the degradation of X-ray image quality due to the reflection of X-rays from behind the sensor panel 110 may be avoided. The anti-reflection film 165a, 165b may be formed of a material that absorbs X-rays, e.g., a metal material having a high atomic number, such as W, Ti, etc., without being limited thereto.

The positions of the anti-reflection films 165a, 165b shown in FIGS. 12 and 13 are only shown by way example, and may be anywhere behind the sensor panel 110.

Figure 14:
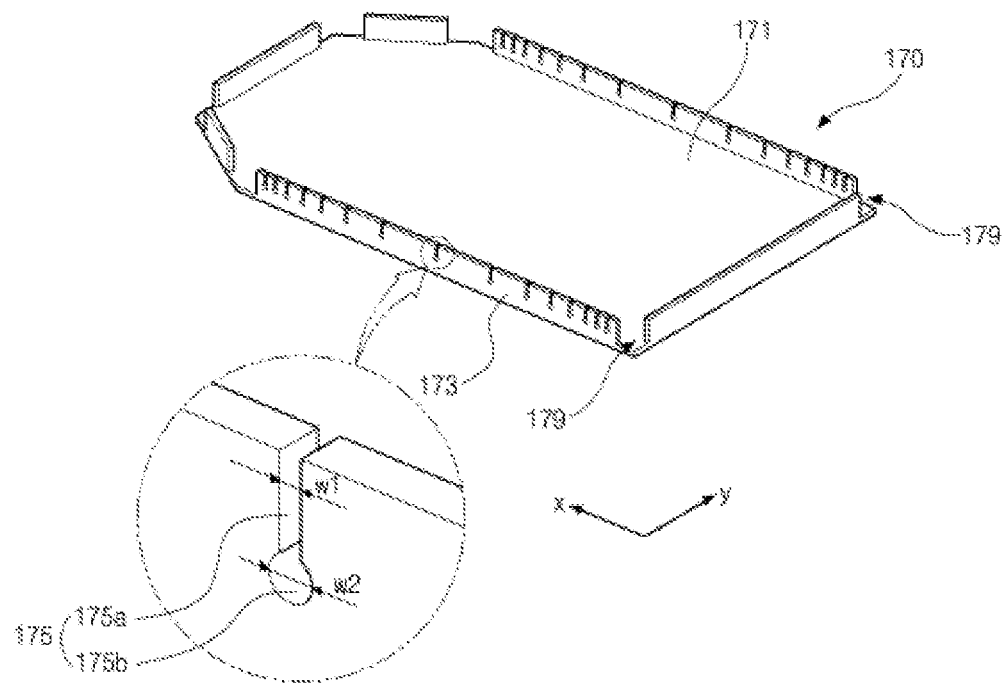
FIG. 14 is a perspective view schematically illustrating a first case according to an embodiment of the present invention.

A first case 170 will now be described in more detail in connection with FIG. 14. FIG. 14 is a perspective view schematically illustrating the first case 170 according to an embodiment of the present invention.

Referring to FIG. 14, the first case 170, located in front of the sensor panel 110, serves as a window cover that is shaped like a box with the rear side open and is transparent to X-rays. The sensor assembly 105 may be received in the internal space above the bottom floor of the first case 170.

The first case 170 may be combined with the sensor assembly 105 using an adhesive 113 that is transparent to radiation. As the adhesive 113, for example, OCA or foam tape may be used, without being limited thereto.

The first case 170 having such a structure may protect the sensor assembly 105, in particular the front of the sensor panel 110, from the external environment.

In particular, the first case 170 in accordance with an embodiment of the present invention serves to define and limit the overall bendability of the intraoral sensor 100 depending on its physical structure, such as the texture, shape, etc.

In this regard, the first case 170 may be made of a highly bendable and high-strength material. For example, the first case 170 may be made of resin, flexible glass or FRP, but is not limited thereto. In addition, the first case 170 may be about 0.1 to 0.5 mm thick, but is not limited thereto.

Because the first case 170 is formed of such a material, the sensor assembly 105 may limit its bending to the range that falls within the bendability of the first case 170. This may prevent the sensor panel 110, which is a key component, from breaking when the sensor assembly 105 is bent excessively. Furthermore, since the intraoral sensor 100 is bendable within a limited range, the distortion of images may be minimized.

The first case 170 may include a base part 171 and side walls 173 that bend orthogonally and protrude backwards from the edges of the base part 171.

The base part 171 may be formed to be substantially planar. Preferably, the side walls 173 may not be formed at the corners of the base part 171. In other words, the neighboring side walls 173 may be disconnected and separated at the corners of the base part 171, meaning that there may be gaps 179 between neighboring side walls 173.

As such, the side walls 173, discontinuously formed along the edges of the base part 171 with gaps 179 at the corners of the base part 171 where neighboring side walls 173 meet, may reduce the occurrence of structural resistance at the corners of the first case 170 and may prevent the first case 170 from breaking due to the concentration of stress at the corresponding parts while the intraoral sensor 100 is being bendable.

Additionally, grooves 175 may be vertically formed in the side walls 173.

In this regard, more specifically, corresponding grooves 175 are formed in the two opposite side walls 173 located along the x-axis, which is the major axis for the rectangular first cover 170, and in particular, the intervals at which the grooves 175 are formed become narrower as the grooves 175 are located farther from the center of the corresponding side wall 173.

With the grooves 175 formed as described above, the extent of bending changes depending on the position along the x-axis. In other words, the narrower the intervals between the grooves 175, the more the corresponding part is bendable, that is, the wider the intervals between the grooves 175, the less the corresponding part is bendable.

Accordingly, the first case 170 has a property such that the extent of bending increases moving toward either end from the center along the x-axis, and such a property is applied to the intraoral sensor 100.

As such, by adjusting the bending property according to the position, the patient's discomfort during an intraoral scan may be more effectively relieved.

In other words, during the intraoral scan, the end parts, rather than the center part of the intraoral sensor 100, mostly come into contact with tissues in the mouth and cause pain. Therefore, increasing the bendability of the end parts helps relieve the patient's discomfort. A part nearer the center part is characterized in that it is less bendable, which helps to minimize overall image distortion attributable to bending.

Although the grooves 175 are formed in the side walls 173 along the major axis in the above embodiment, the grooves 175 may be formed in the side walls 173 along the minor axis, if necessary, and the intervals between the grooves 175 may be adjusted.

The grooves 175 formed in the side walls 173 have a form such that they vertically extend from the top of the side walls 173. The grooves 175 may each include a first groove part 175a, extending down from the top, and may substantially have a constant first width w1 and a second groove part 175b located below the first groove part 175a. At least a portion of the second groove part 175b may be formed to have a second width w2, which is wider than the first width w1.

The second groove part 175b may have various forms, and in an embodiment of the present invention, it is assumed that the second groove part 175b may be shaped like a round circle.

As such, forming the second groove part 175b of the side wall 173 to have a relatively wide width w2 may help prevent the bottom part of the grooves 175 on the side walls 173 from breaking while the intraoral sensor 100 is bending, and may widen the groove 175 while the intraoral sensor 100 is bending, thereby improving its bendability.

Unlike what is shown in the drawings, the grooves 175 may extend to a portion of the base part 171, in which case they still work the same way. Furthermore, if necessary, a plurality of extra grooves may be formed in at least one of the sides of the base part 171, i.e., in at least one of the side with which the sensor panel 110 comes into contact and the other side, in a direction perpendicular to the length direction of the intraoral sensor 100, and the intervals between the extra grooves may also become narrower the closer they are located to the ends from the center. In this case, the extra grooves may not have to pass through the base part 171, and especially, may have a depth equal to or less than the thickness of the base part 171 when formed in the inner side of the base part 171, and may have a tapering form in which the width becomes wider the more closely they are located to the outside of the base part 171.

Turning back to FIGS. 1 to 4, the rear-side support 180 in accordance with an embodiment of the present invention may be located behind the sensor assembly 105, and may serve as a grip post that supports the intraoral sensor 100 during an intraoral X-ray imaging to contact a finger of the user or to be connected to machinery, such as extension cone paralleling (XCP) machinery.

As shown in FIG. 4, the rear-side support 180 may include a body frame 181, a contact part 183, located below and connected to the body frame 181 and having the form of a plate that extends to the outside, and a lead-in port 185, passing through the rear-side support 180 from one side of the body frame 181 to the contact part 183. The rear-side support 180 may be formed of a high-strength resin material, such as PC, ABS, etc., without being limited thereto.

The body frame 181 may be comprised of an upper part 181a and a lower part 181b, located below the upper part 181a, and indented inwards, the width of the upper part 181a being wider than that of the lower part 181b, thus making the sides of the rear-side support 180 stepped, without being limited thereto.

The contact part 183 may be connected to the lower part 181b of the body frame 181 and may be located to correspond, without being limited thereto, to the center part of the sensor assembly 105, and may occasionally be located away from the center part. The front of the contact part 183 tightly contacts the bottom of the sensor assembly 105 and supports the back of the sensor assembly 105. Accordingly, the bending extent of the center part of the sensor assembly 105, supported by the contact part 183, may be limited more than the other parts, in particular both ends of the major axis. The contact part 183 may be held onto the bottom of the sensor assembly 105 through a combining member, e.g., an adhesive, or through a combining hole formed in the contact part 183 and the bottom of the sensor assembly 105 (e.g., PCB 130) by inserting a fastening member into the combining hole.

As a result, the center part of the intraoral sensor 100 corresponding to the contact part 183 may bend less while the surrounding parts bend relatively more, thereby relieving the discomfort of the patient and also minimizing image distortion. As such, the rear-side support 180 may be able to limit the bending extent of the intraoral sensor 100 as well as control the bendability depending on the position.

The transmission cable 210 is inserted into the lead-in port 185. One end of the lead-in port 185 may be located in one side of the body frame 181, and the other end of the lead-in port 185 may be located in the bottom of the contact part 183. The other end of the lead-in port 185 is located to correspond to the input/output pad unit 135.

The transmission cable 210 inserted into the lead-in port 185 may be electrically connected to the input/output pad unit 135 at the other end of the lead-in port 185.

For electrical connection between the transmission cable 210 and the input/output pad unit 135, Anisotropic Conducting Film (ACF), wire bonding, soldering, etc., may be used.

As described above, the contact part 183 tightly contacts the back of the sensor assembly 105 to support the rear part of the sensor assembly 105, thereby achieving a reliable electrical connection between the transmission cable 210 and the sensor assembly 105.

Figure 15:
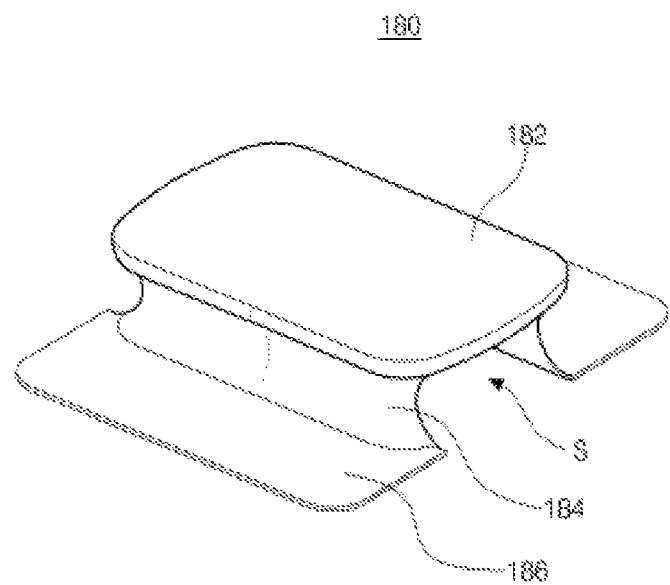
FIG. 15 is a perspective view schematically illustrating a rear-side support according to an embodiment of the present invention.

In the meantime, the rear-side support 180 may be formed in a different shape from what is described above, for example, in a shape defining an internal space S extending downwards like a pipe, as shown in FIG. 15. Specifically, the rear-side support 180 may include a cover part 182, defining the internal space S, side walls 184, and contact parts 186 bending and extending outwards from the side walls 184, and may thus be shaped like a box that is open in the top-down direction. The rear-side support 180 may be formed to have an open shape with at least one side open to the outside, and the transmission cable 210 may be drawn out through the open side. The internal space S may be filled with an insulating material after the transmission cable 210 and the input/output pad unit 131 are connected, thereby protecting the connecting part between the transmission cable 210 and the input/output pad unit 131 and fixing the rear-side support 180 onto the sensor assembly 105.

In the meantime, the aforementioned components, namely the sensor panel 110, the first case 170 in front of the sensor panel 110, and the rear-side support 180 behind the sensor panel 110, are combined together and modularized. To more firmly combine the components, a second case 200 may be used. The second case 200 may be a molded case. Referring to FIG. 4, the second case 200 may be formed to cover part or all of the front and outer sides of the first case 170, the back of the sensor assembly 105, and part or all of the contact part 183. The second case 200 may be formed to have a certain thickness from the back of the contact part 183 and to cover portions of the sides of the lower part 181b. In other words, the second case 200 may be formed such that parts other than the part of the lower part 181b of the rear-side support 180 may be exposed. Alternatively, in the case of the rear-side support 180 of FIG. 15, it is possible for the second case 200 to cover a portion or all of the contact part 186, and if necessary, a portion of the side walls 184.

The second case 200 may be formed of, for example, a resin material, without being limited thereto. Especially, taking into account the property of bending to a limited extent, a material having a shore hardness of about D 10 to 20 may be used for the second case 200, without being limited thereto.

As such, including the second case 200 may help combine the sensor assembly 105, the first case 170, and the rear-side support 180 more firmly, and may more reliably secure the electrical connection between the sensor assembly 105 and the transmission cable 210. The use of a material bendable to a limited extent for the second case 200 may limit the overall bending extent of the intraoral sensor 100, depending on the purpose.

Figure 16:
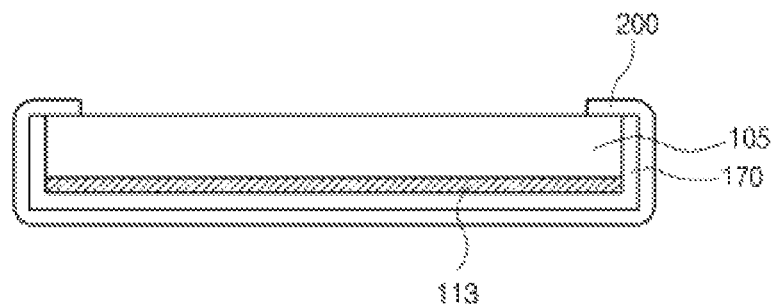
FIG. 16 is a cross-sectional view schematically illustrating a second case according to an embodiment of the present invention.

In another example, as shown in FIG. 16, the second case 200 may have a form that wraps the whole first case 170 and covers the back edges of the sensor assembly 105. In this case, the second case 200 may use a soft material, such as silicon, having a shore hardness of about A 30 to 50, without being limited thereto, and may be formed only to cover the metal sheet (see 160 of FIG. 8), without being limited thereto.

By applying a molding method to the intraoral sensor 100 having the second case 200, an intraoral sensor 100, the exterior of which is covered by the housing 190 as shown in FIGS. 1 and 2, may be manufactured.

The housing 190 serves to enclose and protect the exterior of the intraoral sensor 100. The housing 190 may be formed to cover the entire second case 200. Accordingly, the housing 190 is formed to cover the exterior of the first case 170 and the back of the sensor assembly 110, and if necessary, may be formed to additionally cover the rear-side support 180.

The housing 190 may be formed to fill at least a part of the lead-in port 185 of the rear-side support 180. For example, the housing 190 may be formed to cover an end of the lead-in port 185 that is located on one side of the rear-side support 180, as shown in FIG. 1. Furthermore, with respect to the transmission cable 210 extending to the outside from the lead-in port 185, the housing 190 may be formed to extend a certain length to wrap a part of the transmission cable 210 from an end of the lead-in port 185. In other words, the housing 190 may include an extension 191 to wrap the transmission cable 210.

If a part of the transmission cable 210 extending to the outside from the lead-in port 185 is covered with a cover formed of a material from the same family to which the material of the housing 190 belongs, the cover may be enclosed by the extension 191. The cover may be formed to extend up to the connection part between the transmission cable 210 and the sensor assembly 105. Specifically, a certain length of the transmission cable 210 passing through the lead-in port 185 from the connection part of the sensor assembly 105 may be wrapped with the cover. Alternatively, the entire length of the transmission cable 210 may be wrapped by the cover.

In the case that the housing 190 and the cover are formed of materials from the same family, the strength of the junction between the molded housing 190 and the cover may be enhanced, and as a result, the connection between the transmission cable 210 and the intraoral sensor 100 may be more robust.

In the embodiment of the present invention, the housing 190 may be formed of a soft material, e.g., silicon or urethane. More particularly, as the soft material for the housing 190, a material having a shore hardness of about A 30 to 50 may be used, without being limited thereto.

The use of the soft housing 190 as described above may help greatly in relieving the pain felt by the patient during an intraoral scan. In other words, using a soft material for the housing 190, which is the outermost component of the intraoral sensor 100 that comes into direct contact with intraoral tissues, feels soft to the patient using the intraoral sensor 100, thereby effectively relieving the pain felt by the patient. The intraoral sensor 100 covered with the housing 190 may have a thickness of about 5 mm or so, except the rear-side support 180, without being limited thereto, taking into account its characteristics.

The intraoral sensor 100 in accordance with the embodiment of the present disclosure as described above may have various structural modifications, which will now be described in connection with FIGS. 17 and 18.

Figure 17:
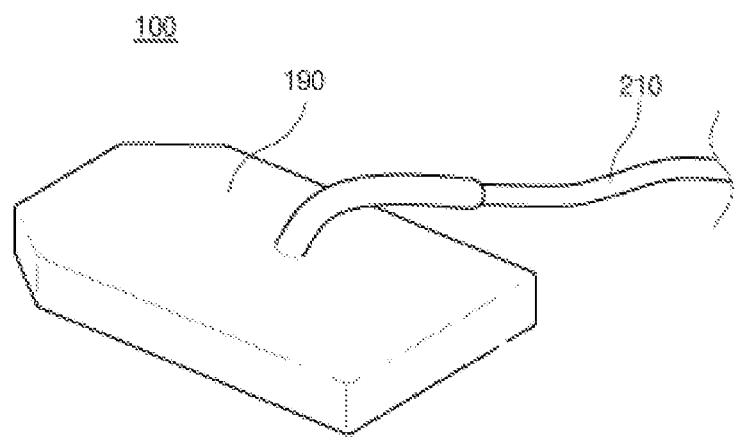
FIGS. 17 and 18 are perspective and cross-sectional views, respectively, of an intraoral sensor according to another embodiment of the present invention.
Figure 18:
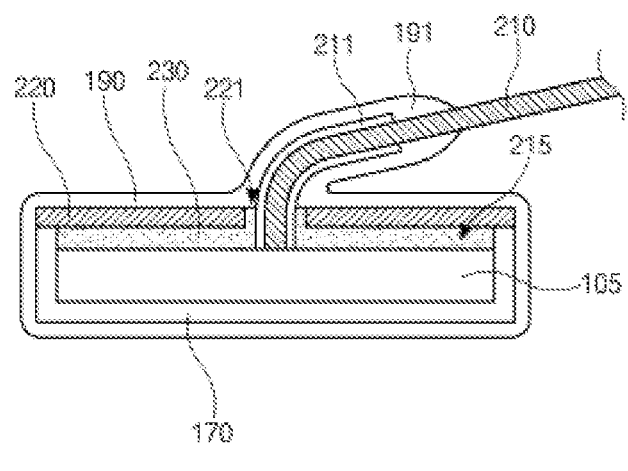

FIGS. 17 and 18 are perspective and cross-sectional views, respectively, of the intraoral sensor 100 according to another embodiment of the present invention.

The intraoral sensor 100 of FIGS. 17 and 18 may, with some exceptions, include components that are the same or similar to those of the embodiment described above, and the same or similar components will not be further described herein.

The intraoral sensor 200 in the present embodiment may include the sensor assembly 105, the first case 170, and the housing 190.

Moreover, the intraoral sensor 100 may include a protective cover 220 in the back of the sensor assembly 105. The protective cover 220 may be formed to be substantially planar, without being limited thereto.

The protective cover 220 may protect the components of the intraoral sensor 100 from behind.

Furthermore, the protective cover 220 may be formed to define and limit the overall bendability of the intraoral sensor 100 together with the first case 170.

For this, the protective cover 220 may be made of a low-elasticity, high-strength material, for example, polycarbonate (PC), having a thickness of 0.1 to 0.5 mm, without being limited thereto.

In addition, an opening 221 through which the transmission cable 210 passes may be formed in the center of the protective cover 220.

The transmission cable 210 is drawn in through the opening 221 in the protective cover 180 and is connected to the PCB (see 130 of FIG. 7).

The protective cover 220 and the sensor assembly 105 may be formed to be separated from each other.

Specifically, a separation gap 215 may be formed between the protective cover 220 and the sensor assembly 105, and may be connected to the opening 221 to draw the transmission cable 210 into the separation gap 215 through the opening 221.

In this case, the separation gap 215 may be filled with a filler 230. The filler 230 may fill the separation gap 215 up to the opening 221.

The filler 230 may use a resin that is hardened by heat or ultraviolet (UV) radiation, e.g., an epoxy resin. The filler 230 is injected into the separation gap 215, and is then hardened by heat or UV radiation.

Because the separation gap 215 is filled with the filler 230, the electrical connection of the transmission cable 210 may be more reliable.

In another example, an adhesive may be used to fill the separation gap 230, instead of the filler 215. The adhesive is a means of attaching the sensor assembly 105 and the protective cover 220 to each other, and with the adhesive, the transmission cable 210 may be reliably fixed to the sensor assembly 105. For reference, reference numeral 211 denotes a cover, a part or all of which is covered by the housing 190 and which wraps a part of the transmission cable 210, and the cover may be made of a resin material from the same family as that of the housing 190.

When an intraoral sensor having the structure described in the above embodiment of the present invention is inserted into the mouth of a patient to take X-ray imagings of an intraoral structure, such as teeth and surrounding tissues, the intraoral sensor may be bendable in relation to the shape or position of the intraoral structure, and as a result, the shape of the intraoral structure may be changed, as will be described later in connection with FIGS. 19a and 19b. The intraoral sensor 100 bends differently at different positions due to the external force applied to the intraoral structure of the patient and the repulsive force from the intraoral structure, and may bend differently within the limit of elasticity in relation to the arrangement of the intraoral structure at each position. Accordingly, an unfamiliar feeling and pain that might be felt by the patient may be greatly relieved, and furthermore, image distortion is less likely to occur.

Figure 19A:
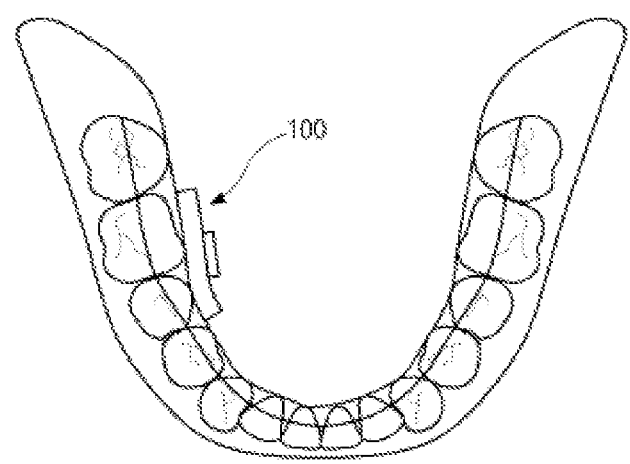
FIGS. 19A and 19B schematically illustrate a change in the shape of an intraoral sensor according to the position in the mouth, according to the present invention.
Figure 19B:
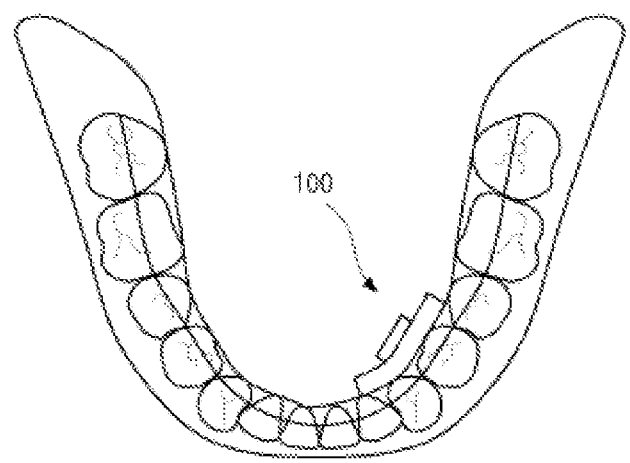
Figure 20:
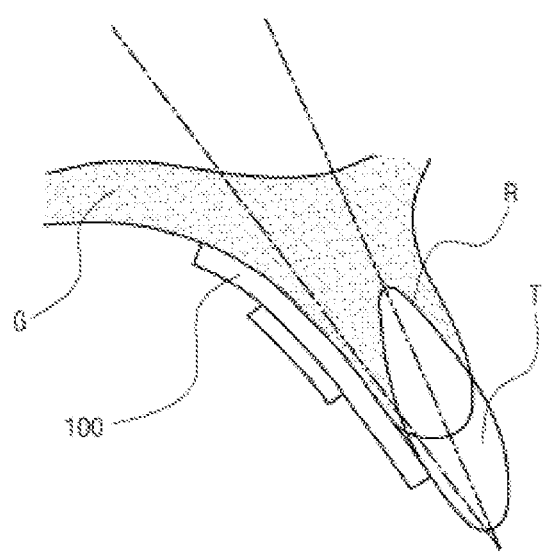
FIG. 20 schematically illustrates a scan of the root of the teeth using an intraoral sensor, according to the present invention.

FIGS. 19A, 19B, and 20 illustrate the taking of intraoral X-ray imaging using the intraoral sensor 100 according to the present invention. For reference, FIGS. 19A and 19B illustrate intraoral X-ray imaging of the upper and lower jaws, respectively, and FIG. 20 illustrates an X-ray imaging of a root of a tooth.

The intraoral sensor 100 in accordance with the present invention is bendable along the intraoral structure during the intraoral X-ray imaging, and thus, substantially the entire front of the intraoral sensor 100 makes tight contact along the intraoral structure, e.g., the teeth T and gums G, which cover the roots of the teeth R. At this time, a part of the intraoral sensor 100 may be separated from the intraoral structure at some X-ray imaging positions, but the resultant gap is 3 mm or less.

Accordingly, compared to a common rigid intraoral sensor, the intraoral sensor of the present invention may relieve the pain of the patient while being placed relatively closer to the object of the X-ray imaging, such as the root of the teeth R, thereby obtaining more accurate X-ray images.

Furthermore, in conjunction with FIGS. 19A and 19B, the intraoral sensor 100 according to the present invention may be bendable along the intraoral structure during X-ray imaging of the upper and lower jaws and an occlusion state, ensuring that substantially its entire front comes into tight contact along the entire shape of the intraoral structure, and that even if a part of the front of the intraoral sensor 100 is separated from the intraoral structure, the gap is 3 mm or less.

Accordingly, compared to a common rigid intraoral sensor, the intraoral sensor of the present invention may relieve the pain of the patient while being placed relatively closer to an object to be scanned, such as the teeth, thereby obtaining more accurate X-ray images of the occlusion.

Figure 21:
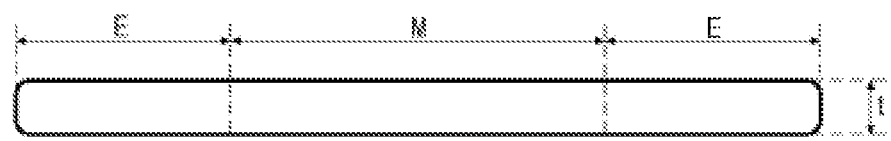
FIGS. 21 and 22 schematically illustrate a bending property of an intraoral sensor, according to the present invention.
Figure 22:
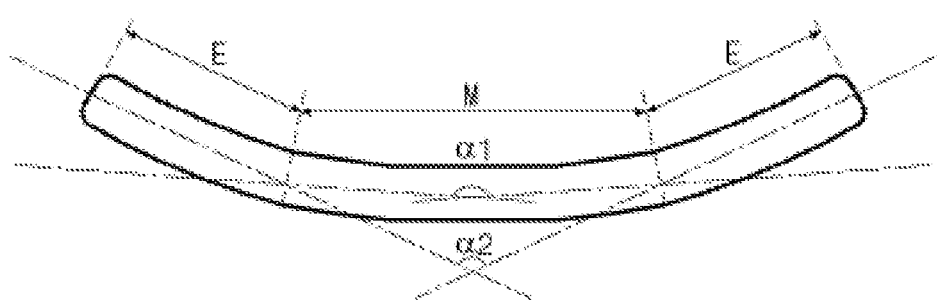

FIGS. 21 and 22 schematically illustrate the bendability of an intraoral sensor according to the present invention. For reference, FIGS. 21 and 22 are plan views of an intraoral sensor along the major axis, according to the present invention.

The intraoral sensor according to the present invention remains flat when no particular force is applied thereto, as shown in FIG. 21, the thickness t, except the rear-side support, being 2 to 8 mm, preferably 3 to 7 mm or so.

Furthermore, the intraoral sensor according to the present invention is bendable along the intraoral structure during an intraoral X-ray imaging, in which case, as discussed above, the intraoral sensor is relatively less bendable at its center area, which is a first area M corresponding to the rear-side support, than at its ends, which are second areas E distinct from the first area M with respect to the major axis. The area occupied by the first area M is about 30 to 70% of the whole area.

Accordingly, the first and second areas M and E of the intraoral sensor in accordance with the present invention are bendable at different angles, the specific values of which are varied by the shape or position of the intraoral structure and by the force applied to the intraoral sensor, but, for example, the first area M may be bendable at angle $\alpha 1$ ranging from 160° to 180°, preferably from 170° to 180°, and the second area E may be bendable at angle $\alpha 2$ ranging from 110° to 180°, preferably from 120° to 180°.

As described above, the intraoral sensor in accordance with embodiments of the present disclosure may be formed to have different bending extents in relation to the position of the intraoral structure, thereby relieving the discomfort of the patient.

The intraoral sensor may use a first case, which is located in front of the sensor panel for containing the sensor panel and has a property of limited bendability. Accordingly, the intraoral sensor bends within a limited range to enable a bendable X-ray intraoral sensor to be implemented, which may minimize image distortion and significantly relieve the discomfort of the patient.

Furthermore, forming grooves in the side walls of the first case to control the bendability according to the position may help minimize image distortion and more effectively relieve the discomfort of the patient during an intraoral scan.

Moreover, a rear-side support may be arranged behind the sensor panel to limit the bending extent of the center part of the sensor panel pressed by the rear-side support as compared to the surrounding parts of the sensor panel, thereby minimizing image distortion and relieving discomfort of the patient during an intraoral scan.

A molding second case may also be used to combine the components of the intraoral sensor more firmly, and accordingly, the electrical connection between the transmission cable and the intraoral sensor may be reliably achieved.

Furthermore, a soft molded housing may be used to cover the exterior of the intraoral sensor, thereby significantly relieving the discomfort felt by the patient during an intraoral scan.

Moreover, input/output pads may be arranged to correspond to the central area of a printed circuit board (PCB), where stress is minimized when bending occurs, such that defects of the input/output pads caused by bending may be minimized.

Furthermore, grounding patterns may be formed on edges of the PCB and a grounding sheet connected to them may be combined with the sensor assembly, to reduce the incidence of defects caused by static electricity.

In addition, an anti-X-ray reflection film may be arranged on the back of the sensor panel to alleviate a phenomenon of back-scattering.

Consequently, according to the present invention, an intraoral sensor having a property of limited bendability may be effectively implemented, and may thus minimize the patient's discomfort.

The invention claimed is:

1. An intraoral sensor for intraoral X-ray imaging, comprising:
   a sensor panel for generating electric signals from X-rays, wherein the sensor panel includes: a semiconductor substrate having a thickness of 100 um or less, a photoelectric transducer element formed on the semiconductor substrate, and a scintillator layer covering the photoelectric transducer element;
   a first case for covering a side of the sensor panel on which the X-rays are incident;
   a housing for covering the sensor panel and the first case;
   an elasticity adjustment member covering a side of the sensor panel that is opposite a side on which the X-rays are incident; and
   a flexible printed circuit board (PCB) covering the elasticity adjustment member, wherein the intraoral sensor is bendable along an intraoral structure during an intraoral X-ray imaging, and has a first area corresponding to a part along a major axis and a second area corresponding to a remaining part, the first area and the second area bending to different extents.

2. The intraoral sensor of claim 1, further comprising:
a flexible layer formed in the semiconductor substrate on a side opposite the scintillator layer.

3. The intraoral sensor of claim 1, further comprising:
a first adhesive located between the sensor panel and the elasticity adjustment member; and
a second adhesive located between the elasticity adjustment member and the flexible PCB.

4. The intraoral sensor of claim 1, further comprising: a rear-side support located on the flexible PCB, wherein the housing covers a part or all of the rear-side support.

5. The intraoral sensor of claim 4, wherein the rear-side support is positioned so that the first area is bendable to a lesser extent than the second area.

6. The intraoral sensor of claim 4, further comprising:
a transmission cable electrically connected to the flexible PCB through the rear-side support.

7. The intraoral sensor of claim 6, further comprising:
an input/output pad unit provided in a center of the major axis of the flexible PCB along a minor axis of the flexible PCB and is electrically connected to the transmission cable.

8. The intraoral sensor of claim 1, wherein the first case has a physical shape that enables the first area to bend to a lesser extent than the second area.

9. The intraoral sensor of claim 1, further comprising:
a rear-side support provided on a side of the sensor panel that is opposite a side on which X-rays are incident, a part or all of the rear-side support being covered by the housing.

10. The intraoral sensor of claim 9, wherein the rear-side support is positioned so as to enable the first area to bend to a lesser extent than the second area through its arrangement position.

11. An intraoral sensor for intraoral X-ray imaging, the intraoral sensor, comprising:
a sensor panel for generating electric signals from X-rays;
a housing for covering the sensor panel;
an elasticity adjustment member covering a side of the sensor panel that is opposite a side on which the X-rays are incident; and
a flexible printed circuit board (PCB) covering the elasticity adjustment member,
wherein the intraoral sensor is bendable along an intraoral structure during an intraoral X-ray imaging, and has a first area corresponding to a part along a major axis and a second area corresponding to a remaining part, the first area and the second area bending to different extents.

12. The intraoral sensor of claim 11, wherein the first area includes a center along the major axis, and the first area bends to a lesser extent than the second area.

13. The intraoral sensor of claim 11, wherein the first area occupies 30 to 70% of an entire area.

14. The intraoral sensor of claim 11, wherein the first area bends at an angle ranging from 160° to 180°.

15. The intraoral sensor of claim 11, wherein the second area bends at an angle ranging from 110° to 180°.

16. The intraoral sensor of claim 1, wherein the rear-side supports protrude from the rear side.

17. The intraoral sensor of claim 16, wherein a thickness of the intraoral sensor is 2 to 8 mm, except the rear-side support.

* * * * *